United States Patent [19]

Kageyama et al.

[11] 3,992,442
[45] Nov. 16, 1976

[54] PROCESS FOR THE CONTINUOUS PRODUCTION OF SORBIC ACID

[75] Inventors: Osamu Kageyama, Ohmiya; Manabu Kai; Tadayuki Mitani, both of Ohimachi; Akira Asahi; Sadao Sasaki, both of Arai, all of Japan

[73] Assignee: Daicel Ltd., Osaka, Japan

[22] Filed: Dec. 13, 1974

[21] Appl. No.: 532,578

[30] Foreign Application Priority Data

Dec. 14, 1973  Japan............................. 48-140583

[52] U.S. Cl............................................. 260/526 N
[51] Int. Cl.² ........................................ C07C 51/00
[58] Field of Search ............................. 260/526 N

[56] References Cited

UNITED STATES PATENTS 3,759,988  9/1973  Kunstle ........................... 260/526 N Primary Examiner—Vivian Garner
Attorney, Agent, or Firm—Woodhams, Blanchard and Flynn

[57] ABSTRACT

A process for manufacturing sorbic acid in a continuous manner which comprises preparing a polyester from ketene and crotonaldehyde and then decomposing the polyester with hydrochloric acid in a multiple reactor system under such conditions that the degree of the decomposition of the starting polyester in each reactor is maintained at either (1) not more than 45 percent, or (2) not less than 90 percent.

3 Claims, 1 Drawing Figure

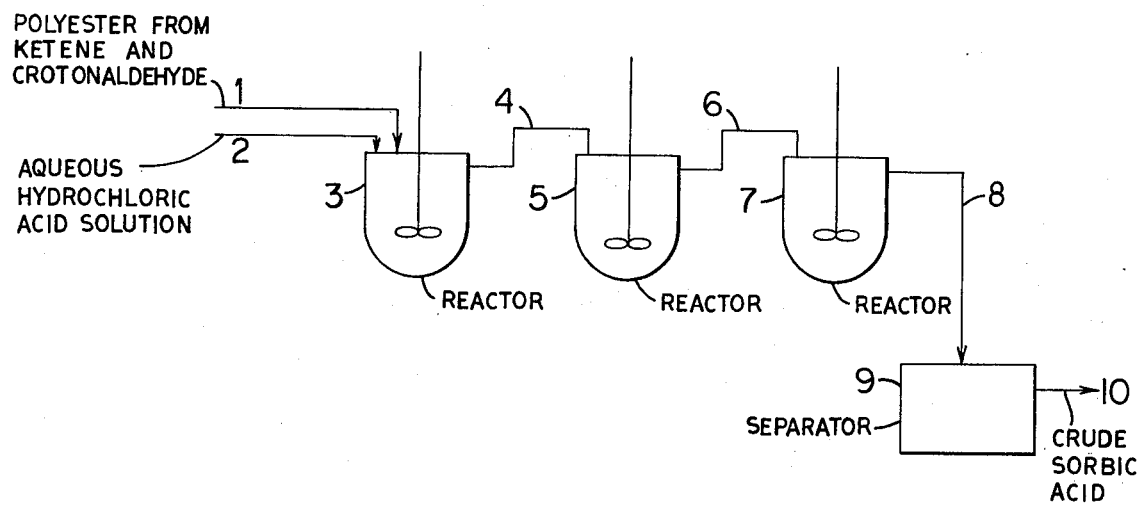

PROCESS FOR THE CONTINUOUS PRODUCTION OF SORBIC ACID

BACKGROUND OF THE INVENTION

1. Field of the Invention

This invention relates to a process for continuously manufacturing sorbic acid by decomposing, with hydrochloric acid, a polyester which has been obtained by the polymerization reaction of ketene and crotonaldehyde.

2. Description of the Prior Art

Compared with a batch process, a continuous process for manufacturing chemical products has a number of technical and economic advantages, for example, the reaction conditions are capable of being kept in an optimum steady state, control of the operations can be carried out by a few operators and the quality of the products is more uniform and stable. Because of these advantages, it has long been desired to provide a continuous process for producing sorbic acid from a polyester which has been obtained by polymerizing ketene and crotonaldehyde.

As one of processes above-mentioned, a single-stage continuous reaction process for manufacturing sorbic acid was proposed in Japanese Patent Publication No. 24537/1972. We have carried out experiments concerning this process, in which continuous decomposition of the polyester with 28% hydrochloric acid was carried out in a single reactor under the conditions of (1) a reaction temperature of 82° C and (2) an average residence time of 60 min. The test results were as follows:

According to our experiments, the reaction in a single reaction vessel, tended to leave a small quantity of undecomposed polyester in the reaction mixture, which in turn made the reaction mixture (slurry) slow to flow in the reactor. Further, the process yielded crude sorbic acid which, when purified and analyzed by the method described in the examples below, showed a degree of transparency which was about 10% less than that of sorbic acid produced by batch processes. Moreover, back mixing occurred in the reaction vessel which eventually resulted in a relatively low volumetric efficiency, thereby necessitating the use of a comparatively larger reactor. Finally, this process caused the range of the residence time of the reaction mixture in the reactor to be so large that the sorbic acid thus produced had undesirably variable properties.

We have studied a modified continuous process, in which the polyester is decomposed, in a stepwise fashion, in a plurality of reaction vessels. This multiple reactor system, however, encounters serious technological problems because the reactants tend to solidify into lump form. Therefore it is impossible to obtain a sufficient flow and agitation of the reactants, so that clogging occurs in one or more reactors, a nonuniform reaction occurs, the reactants adhere onto the walls of the reactors, it is impossible to transfer the reactants from one reactor to another and other troubles. We have determined that in a continuous process for decomposing such a polyester the reactants must be prevented from solidifying, particularly during operations of transferring the reaction mixture from one vessel to another.

In addition, we have also found that in the foregoing modified continuous process, the polyester to be decomposed with hydrochloric acid is caused to be dispersed in the acid by agitation. At the outset of the decomposition reaction some sorbic acid is produced, and the dispersed mixture of starting materials (polyester and hydrochloric acid) and the product sorbic acid form a liquid-liquid heterogeneous mixture. As the polyester decomposes further, the thus-formed sorbic acid causes the reaction mixture to increase in apparent viscosity. As a result, it becomes difficult to maintain the remaining starting polyester in a finely divided dispersed state in the reaction mixture. Consequently, the sorbic acid produced in this nonuniform nonhomogeneous reaction mixture tends to solidify as a solid mass, thereby making it difficult to continuously operate a multiple reactor system.

On the other hand, however, when the decomposition has proceeded further to such an extent that unreacted polyester is scarcely present, i.e. the reaction mixture contains less than 10% of the original amount of starting polyester, the thus-formed sorbic acid particles disperse in the hydrochloric acid completely to form a slurry having excellent fluidity, and which is easily agitatable and flowable.

DETAILED DESCRIPTION OF THE INVENTION

In order to overcome these serious technological problems, we have further studied the foregoing process for manufacturing sorbic acid, particularly to discover what physical changes occur in the reaction mixture (consisting essentially of starting polyester, hydrochloric acid aqueous solution and product sorbic acid). We have discovered that the foregoing reaction mixture is capable of becoming viscous, nonagitatable and of poor fluidity, leading to solidification, when from 45 to 90 weight percent of the starting polyester has been decomposed with hydrochloric acid. We have discovered that the foregoing process can be effectively carried out in a multiple reactor system, provided that the average conversion of polyester is increased stepwise so as to carry out the decomposition reaction continuously and perfectly.

We have successfully decomposed polyester, to form sorbic acid, continuously in a multiple reactor system under conditions, particulars of which are explained in the examples that follow, which are optimum in terms of reaction temperature, hydrochloric acid concentration and residence time of the reaction mixture. The continuous decomposition is carried out so that the percentage of decomposed polyester, based on the original starting amount of polyester, in the reaction mixture leaving any reaction vessel is either not more than 45% or not less than 90%, i.e., the average conversion of polyester in one reactor must be either not more than 45% or not less than 90%.

BRIEF DESCRIPTION OF THE DRAWING

The drawing is a schematic illustration of a system employing three reactors for carrying out the process of the invention.

DETAILED DESCRIPTION OF THE INVENTION

As shown in the drawing, a polyester, obtained by the known reaction of ketene and crotonaldehyde, is fed continuously through the conduit 1 into the first reactor 3, and hydrochloric acid is also charged continuously through the other conduit 2. The conditions of operation, temperature, time, HCl concentration, are maintained at levels such that not more than 45% of the polyester is decomposed in reactor 3.

The resulting flowable solution including sorbic acid product is continuously flowed through the conduit 4 into the reactor 5, where the conditions of operation are such that polyester is further decomposed so that more than 90%, preferably 95%, of the polyester has been decomposed by the time the reaction mixture leaves reactor 5. This flowable reaction solution is finally transferred through the conduit 6 into the reactor 7, where the solution is aged so to complete decomposition of the polyester. The resulting mixture mainly composed of crude sorbic acid and hydrochloric acid is sent through the conduit 8 into the separator 9, in which the hydrochloric acid is filtered and washed with water, and the crude sorbic acid is transferred through the conduit 10 to the purification process that follows.

The decomposition of the starting polyester, according to our invention requires at least two stages. It can be conducted with a set of two reactors so that each reactor constitutes one stage. In fact, the greater the number of the reactors, the better is the quality of sorbic acid that is produced. However, for economic reasons, a set of two or three reactors are preferably employed because these numbers of reactors are enough to give a reaction solution of such a good quality that highly pure sorbic acid can be obtained by purification of the final reaction solution.

The reactors are of any suitable convention type for effecting a steady flow of the reaction mixture therethrough, with agitation of the reaction mixture.

According to this invention, the concentration of hydrochloric acid, the reaction temperature and residence time of reaction mixture in the reactor are selected and maintained so that the average decomposition rate of the polyester in each reactor can be maintained at either (1) not more than 45 percent, or (2) not less than 90 percent.

The critical feature of the invention is that in the first reaction stage, i.e. the reactor 3 in the drawing, not more than 45 wt. %, preferably from about 10 to 30%, of the starting polyester is decomposed. And in the second reaction stage, i.e. the reactor 5 in the drawing, not less than 90 wt. %, preferably at least 93%, of the starting polyester is decomposed. Thus, referring to the drawing, in reactor 5, the solution fed therein contains not less than 55 wt. % of the original starting polyester and the solution discharged therefrom contains not more than 10% of said polyester.

Further, it will be understood that in order to obtain the foregoing desired decomposition rates, there can be employed many different combinations of the three decomposition rate-determining factors, i.e. hydrochloric acid concentration, reaction temperature and residence time. The desired decomposition rates of the polyester can be obtained using hydrochloric acid concentrations in the range of from 20 to 36% and a reaction temperature in the range of from 60° to 95° C. The appropriate residence time of the solution can be determined, based on the first two factors. In general, higher hydrochloric acid concentrations and higher temperatures increase the decomposition rate.

For example, to obtain a polyester decomposition rate of 30% in the first reactor, appropriate conditions are a hydrochloric acid concentration of 30%, a reaction temperature of 80° C, and a residence time of 8 minutes. To obtain a polyester decomposition rate of 95% in the second reactor, the corresponding conditions in the second reactor are 30%, 86° C and 23 minutes, respectively. It is preferred to use a higher reaction temperature in the second reaction vessel.

In any case, the decomposition of the polyester in both reactors must be carried out strictly within the foregoing ranges of 20 to 36% hydrochloric acid concentration and 60° to 95° C in reaction temperature; otherwise undesirable results will occur. For example, if the hydrochloric acid concentration is below 20% and the reaction temperature is below 60° C, then no decomposition will occur, and conversely if the reaction temperature is over 95° C, a side reaction will occur thereby to produce sorbic acid that is inferior in quality.

The starting polyester, when reacted with hydrochloric acid under the foregoing conditions, will satisfactorily decompose in a very short time without causing any undue difficulty in the continuous operation of the reactors.

A preferred molecular weight of the polyester to be used in this invention is 400 to 4000, which was estimated with gel permeation chromatography.

The amount of hydrochloric acid solution added to the polyester must be more than 2 parts by weight of hydrochloric acid solution to 1 part by weight of polyester so as to facilitate the continuous treatment of the polyester. The upper limit is not critical, but for practical reasons, particularly reactor size, the amount of hydrochloric acid usually does not exceed about 5 times the amount of polyester. Further, the hydrochloric acid can be recycled. This invention is further described by reference to the following illustrative examples:

EXAMPLE 1

Into 1,000 g of crotonaldehyde was added 3 g of zinc chloride as a catalyst and then 248 g of ketene gas was introduced into the solution through a gas dispersing plate at the rate of 40 to 50 g per hour and at a reaction temperature of from 30 to 35° C.

After the reaction was complete, excess crotonaldehyde was distilled off under a reduced pressure of 50 mm Hg abs. to yield 751 g of polyester, which was transparent, rose colored and of high viscosity.

Into the first reactor of a reaction system consisting of two reactors, each of which was provided with a stirrer, there were fed 100 parts by weight per hour of the foregoing polyester and 300 parts by weight per hour of 31% hydrochloric acid. In the first reactor, 20% of the polyester was decomposed under the conditions of a reaction temperature of 70° C and an average residence time of 9.8 minutes. Then the reaction mixture was transferred into the second reactor, where the mixture was reacted at 84° C for an average residence time of 24 minutes, to produce a reaction product containing crude sorbic acid and hydrochloric acid. The polyester decomposition rate of this reaction product was 92 ± 2%, based on the polyester fed into the first reactor.

The reaction was carried out continuously, under the foregoing conditions, for five hours. The resulting reaction product was filtered to yield crude sorbic acid which was washed with water and dried. To 300 g of the resultant crude sorbic acid was added caustic soda to form a solution of about 10% sodium sorbate solution in water. To this solution there was added 15 g of activated charcoal, and the solution was heated with stirring at 60° C for 30 minutes. Thereafter, the activated charcoal was filtered off. To the filtrate was added concentrated hydrochloric acid in quantity sufficient to neutralize the filtrate, which then was cooled to 30° C to precipitate sorbic acid. The sorbic acid was filtered out, washed, and then dried in vacuo at 50° C. A 0.75 g sample of the resultant sorbic acid was dissolved in 10 cc of 1N aqueous caustic soda solution. Its phototransparency was measured by a photospectrometer at 420 m$\mu$. The transparency value was 72% which is similar to that of sorbic acid produced by a high-quality batch process.

EXAMPLE 2

Into the first reactor of a reaction system consisting of three reactors, each of which was equipped with a stirrer, were fed 300 parts by weight per hour of 27.6% hydrochloric acid and 100 parts by weight per hour of the foregoing polyester. In this first reactor, 13.4% of the polyester was decomposed at a reaction temperature of 70.5° C for an average residence time of 9 minutes and 48 seconds, and then the solution was transferred into the second reactor.

In the second reactor, the polyester was decomposed at 86.0° C for 23 minutes in average residence time; the decomposition rate was 95 ± 2%.

In the third reactor, the residual polyester was decomposed at 86.0° C for 8 minutes to yield sorbic acid which is very well stabilized in quality.

Using these conditions, the reaction was effected in the mixing system continuously for 240 hours without any trouble. The reaction mixture was treated in the same way as explained in the Example 1. The resulting sorbic acid was measured for phototransparency at 420 m$\mu$. The value was about 74%.

The embodiments of the invention in which an exclusive property or privilege is claimed are defined as follows:

1. A continuous process for preparing sorbic acid, by decomposing a liquid polyester obtained by reacting ketene and crotonaldehyde, with aqueous hydrochloric acid solution having a concentration of from 20 to 36 percent by weight, comprising the steps of: continuously feeding streams of said liquid polyester and said aqueous hydrochloric acid solution, in a weight ratio of at least 2 parts by weight of said hydrochloric acid solution per one part by weight of said polyester, into a first reaction stage, agitating same to form a uniform liquid reaction mixture and maintaining said reaction mixture in said first stage for a period of time effective to decompose therein not more than 45 weight percent of said polyester, continuously feeding a stream of said reaction mixture leaving the first reaction stage into a second reaction stage, agitating the reaction mixture in the second stage and maintaining said reaction mixture in said second stage for a period of time effective to decompose therein not less than 90 percent by weight of said polyester, the reaction temperature of both the first and second stages being in the range of from 60° to 95° C, discharging the reaction mixture from said second stage and recovering sorbic acid from the reaction mixture.

2. A process as claimed in claim 1, in which the reaction mixture discharged from said second stage is fed into a third reaction vessel and is maintained therein, at from 60° to 95° C, to complete decomposition of said polyester and then recovering sorbic acid from the reaction mixture discharged from the third reaction vessel.

3. A process as claimed in claim 1, in which, in said first reaction stage, from 10 to 30 weight percent of polyester is decomposed.

* * * * *